United States Patent [19]
Coughlin et al.

[11] Patent Number: 4,556,645
[45] Date of Patent: Dec. 3, 1985

[54] ENHANCED CATALYST FOR CONVERSION OF SYNGAS TO LIQUID MOTOR FUELS

[75] Inventors: Peter K. Coughlin, Yorktown Heights; Jule A. Rabo, Armonk, both of N.Y.

[73] Assignee: Union Carbide Corporation, Danbury, Conn.

[21] Appl. No.: 625,373

[22] Filed: Jun. 27, 1984

[51] Int. Cl.$^4$ .................. B01J 29/10; B01J 27/14
[52] U.S. Cl. ...................... 502/66; 502/74; 502/214
[58] Field of Search ............ 502/66, 74, 214, 67; 518/715

[56] References Cited

U.S. PATENT DOCUMENTS

| | | | |
|---|---|---|---|
| 3,013,990 | 12/1961 | Breck et al. | 252/455 |
| 3,354,096 | 11/1967 | Young | 502/74 X |
| 4,086,262 | 4/1978 | Chang et al. | 260/449.6 R |
| 4,157,338 | 6/1979 | Haag et al. | 260/449 R |
| 4,172,843 | 10/1979 | Dwyer et al. | 260/449.6 R |
| 4,180,516 | 12/1979 | Chang et al. | 260/449 R |
| 4,207,248 | 6/1980 | Butter et al. | 260/449.6 R |
| 4,279,830 | 7/1981 | Haag et al. | 518/700 |
| 4,340,503 | 7/1982 | Rao et al. | 252/459 |
| 4,440,871 | 4/1984 | Lok et al. | 502/214 |
| 4,460,698 | 7/1984 | Hensley, Jr. et al. | 502/66 |

FOREIGN PATENT DOCUMENTS

| | | |
|---|---|---|
| 874373 | 2/1979 | Belgium . |
| 2077754 | 6/1981 | United Kingdom . |

OTHER PUBLICATIONS

"The Fischer-Tropsch Synthesis in the Liquid Phase"—Catal. Rev.-Sci. Eng., 21(2), 225-274 (1980), Herbert Kolbel and Milos Ralek, pp. 225, 243-247.

Primary Examiner—Carl F. Dees
Attorney, Agent, or Firm—Alvin H. Fritschler

[57] ABSTRACT

Synthesis gas comprising carbon monoxide and hydrogen is converted to $C_5+$ hydrocarbons suitable for use as liquid motor fuels by contact with a dual catalyst system capable of enhancing the selectivity of said conversion to motor fuel range hydrocarbons and the quality of the resulting motor fuel product. The catalyst composition employs a Fischer-Tropsch catalyst, together with a co-catalyst/support component comprising SAPO silicoaluminophosphate, non-zeolitic molecular sieve catalyst.

32 Claims, No Drawings

ENHANCED CATALYST FOR CONVERSION OF SYNGAS TO LIQUID MOTOR FUELS

STATEMENT

The Government of the United States of America has rights to this invention pursuant to Contract No. DE-AC22-81PC40077 awarded by the U.S. Department of Energy.

BACKGROUND OF THE INVENTION

1. Field of the Invention

The invention relates to the conversion of synthesis gas to hydrocarbons. More particularly, it relates to the conversion of such synthesis gas to $C_5+$ hydrocarbons particularly suitable for use as liquid motor fuels.

2. Description of the Prior Art

It is well known in the art that synthesis gas, i.e., hydrogen and carbon monoxide, can be converted to hydrocarbons in the presence of a variety of transition metal catalysts. Thus, certain Group VIII metals, particularly iron, cobalt, ruthenium and nickel, are known to catalyze the conversion of CO and hydrogen, also referred to as syngas, to hydrocarbons. Such metals are commonly called Fischer-Tropsch catalysts. While the use of nickel preferentially produces methane upon conversion of syngas, the use of iron, cobalt and ruthenium tends to produce hydrocarbon mixtures consisting of hydrocarbons having a larger carbon number than methane, as determined by a number of analytical means including mass spectrographic analysis of individual components and the boiling point curve method. At higher reaction temperatures, all Fischer-Tropsch catalysts tend to produce gaseous hydrocarbons, and it is readily feasible to select processing conditions to produce methane as the principal product. At lower temperatures, and usually at higher pressures, however, iron, cobalt and ruthenium produce hydrocarbon mixtures consisting of larger hydrocarbons. These products usually contain very long straight-chain hydrocarbon molecules that tend to precipitate as wax. Such wax material, boiling well beyond the boiling range of motor fuels, typically constitutes a significant fraction of the product produced in such catalytic conversion operations. For these reasons, therefore, Fischer-Tropsch catalysts have not been advantageously employed recently in the production of liquid hydrocarbon motor fuels, instead commonly producing either principally gaseous hydrocarbons, on the one hand, or hydrocarbons containing an unacceptably large amount of wax on the other. In addition, the gasoline range boiling hydrocarbon fraction that is produced has an unacceptably low octane number.

In light of such circumstances, efforts have been made to improve the performance of Fischer-Tropsch catalysts for use in various desired syngas conversions. For example, the Breck et al. patent, U.S. Pat. No. 3,013,990, discloses the use of zeolitic molecular sieves containing a Fischer-Tropsch catalyst as improved catalyst compositions. Thus, Type A, X and Y molecular sieves loaded with iron or cobalt are shown to be suitable Fischer-Tropsch hydrocarbon synthesis catalysts, as for the production of methanol from syngas. Also with respect to the conversion of syngas, Fraenkel et al., U.S. Pat. No. 4,294,725, teach that zeolites A and Y loaded with cobalt, incorporated by ion exchange and reduced in-situ with cadmium, serve as useful catalysts for synthesis of specific, small carbon number hydrocarbons. Those skilled in the art will appreciate that such catalyst materials tend to be relatively expensive and, in any event, do not produce hydrocarbon products advantageous for use as liquid motor fuels.

Efforts have also been made to improve Fischer-Tropsch catalyst performance by preparing intimate mixtures of Fischer-Tropsch metals, such as iron, with an acidic crystalline aluminosilicate, such as ZSM-5. The Chang et al. patents, U.S. Pat. No. 4,086,262, and U.S. Pat. No. 4,096,163, disclose such catalyst compositions employed in the conversion of synthesis gas to hydrocarbon mixture useful in the manufacture of heating fuels, aromatic gasoline, and chemical intermediates. When it is desired to convert syngas specifically to hydrocarbons boiling in the jet fuel+diesel oil boiling range, however, such as approach is not suitable, experiencing an effective limitation at $C_{10}$ carbon number as was the case using ZSM-5 in methanol conversion, as disclosed in the Owen et al. patent, U.S. Pat. No. 3,969,426.

Another difficulty present in the production of liquid motor fuels, particularly those boiling in the gasoline boiling range, by the conversion of syngas in the presence of Fischer-Tropsch metal catalysts is the tendency of such Fischer-Tropsch metals to characteristically produce straight chain hydrocarbons consisting of a mixture of n-paraffins and n-olefins. The actual mixture obtained will be understood to depend upon the particular metal catalyst and the process conditions employed. In any event, the conversion product will generally contain only small amounts of mono-branched and almost no multi-branched hydrocarbons, as well as very little naphthenes and aromatics. The absence of significant amounts of branched or aromatic, i.e. cyclic, hydrocarbons in the conversion products results in such products having gasoline fractions of very low octane number. Such fractions are not suitable for use as gasoline without the addition of further, expensive refining steps. The larger n-paraffins produced in the $C_{10}-C_{18}$ range by such metal catalysts are, nevertheless, desirable components for incorporation in jet and diesel fuels. However, the presence of some branched hydrocarbon components are also desired in such fractions to enhance the thermal efficiency of the overall process for converting raw syngas to such liquid motor fuels and to reduce the pour point of such fuels. In addition, the accompanying production of hydrocarbon products boiling above the diesel oil range constitutes a recognized economic and marketing burden adversely affecting the desired liquid motor fuel operation.

For the reasons above, the development of improved technology for the conversion of syngas to liquid hydrocarbon fuels is desired in the art. Such improved technology would desirably enable such syngas conversion to be carried out with (1) enhanced branching and aromatization as compared with the present production of predominantly n-paraffins and n-olefins, and (2) enhanced production of desired liquid motor fuels by reducing the formation of methane and/or of heavy hydrocarbon products boiling beyond the boiling range of diesel oil.

It is an object of the invention, therefore, to provide an improved process for the conversion of syngas to liquid hydrocarbon motor fuels.

It is another object of the invention to provide a catalyst composition capable of enhancing the conversion of syngas to such liquid motor fuels.

It is a further object of the invention to provide a process and Fischer-Tropsch catalyst composition for producing liquid motor fuels containing minimal amounts of methane and of heavy hydrocarbon products boiling beyond the boiling range of diesel oil.

With these and other objects in mind, the invention is hereinafter described in detail, the novel features thereof being particularly pointed out in the appended claims.

SUMMARY OF THE INVENTION

Synthesis gas is converted to liquid motor fuels in the practice of the invention by the use of a dual catalyst composition containing a Fischer-Tropsch metal as a component thereof. A non-zeolitic silico-aluminumphosphate molecular sieve catalyst is employed as a co-catalyst/support component. The conversion product exhibits improved selectivity to motor fuel range hydrocarbons and improved quality of motor fuel product.

DETAILED DESCRIPTION OF THE INVENTION

The objects of the invention are accomplished by employing a Fischer-Tropsch metal in combination with a non-zeolitic silico-aluminumphosphate molecular sieve catalyst in the conversion of syngas to liquid hydrocarbons. Contrary to the results of various prior art techniques using Fischer-Tropsch catalysts for syngas conversion, the use of the novel catalyst composition of the invention results in an advantageous production of enhanced quality liquid motor fuels boiling in the gasoline and jet fuel plus diesel oil boiling ranges. As the catalyst composition of the invention is found to have outstanding stability over the course of continuous processing operations, the catalyst composition and the process for its use for syngas conversion, as herein described and claimed, represent a highly desirable and practical approach to the desired production of liquid motor fuels boiling in the gasoline, jet fuel+diesel oil boiling range.

The synthesis gas, or syngas, treated in accordance with the practice of the invention generally comprises a mixture of hydrogen and carbon monoxide, usually together with smaller amounts of carbon dioxide, methane, nitrogen and other components as is well known in the art. Syngas is commonly produced by the partial oxidation of coal, petroleum and natural gas deposits, or by similar gasification of other carbonaceous fuels such as peat, wood and cellulosic waste materials. The hydrogen/carbon oxide volume ratio of such syngas is desirably in the range of from about 0.2/1 to about 6.0/1 prior to conversion to liquid motor fuels as herein disclosed and claimed. This ratio can be adjusted, if desired, by reaction of carbon monoxide with steam in the well-known water-gas shift reaction. If required, sulfur impurities can be removed from the syngas mixture by conventional means known in the art. It should also be noted that the syngas as described herein includes art-recognized equivalents, such as mixtures of carbon monoxide and steam, or of carbon dioxide and hydrogen, that can provide synthesis gas mixture by in-situ reaction under the operating conditions employed.

The dual catalyst composition of the invention, employed as described herein for the conversion of syngas to liquid motor fuels, contains a Fischer-Tropsch metal as a component thereof. Various Group VIII metals known to catalyze the conversion of syngas to hydrocarbons, and commonly referred to as Fischer-Tropsch catalysts, may be employed in the practice of the invention, e.g., nickel and rhodium, iron, cobalt, ruthenium, nickel and rhodium as well as compounds of molybdenum, tungsten, rhenium, thorium and the like. It has been found that, on an overall evaluation basis, the use of iron and particularly of cobalt as the Fischer-Tropsch metal component of the catalytic composition is desirable for purposes of the invention.

The second principal component of the catalyst composition of the invention is a crystalline, microporous silicoaluminophosphate, non-zeolitic molecular sieve catalyst, employed as a co-catalyst and optionally as a support for the metal component of the composition. Such catalyst compositions are known in the art as SAPOs, and are available at Union Carbide Corporation. Detailed descriptions of such SAPOs and of their manner of preparation are contained in U.S. Pat. No. 4,440,871, issued Apr. 3, 1984, which is incorporated herein by reference in its entirety. Individual members of the SAPO class are designated as SAPO-5, SAPO-11, SAPO-17, SAPO-20, SAPO-31, SAPO-34 and the like as will be evident from said patent. For purposes of the invention SAPO-11 and SAPO-31 are generally preferred co-catalyst/support components, although it will be appreciated that other SAPOs, or combinations thereof, may be employed in the practice of the invention. Such SAPOs have been used heretofore as polymerization catalysts to produce high boiling polymerization products and for other purposes, but have not been employed in processes directed to the conversion of syngas to liquid fuels or other products. Various other non-zeolite molecular sieve materials of the SAPO structure class can also be employed for purposes of the inventiion. For example, U.S. patent application, Ser. No. 400,438, filed July 26, 1982, incorporated by reference herein, discloses such SAPO materials preferably characterized by an adsorption of triethylamine of less than 5% by weight at a pressure of 2.6 torr and a temperature of 22° C. More preferably, such materials, also designated in said patent application as SAPO-11, SAPO-31 and the like, where the number in each case refers to its specific preparation as reported in said patent application, are further characterized by an adsorption of cyclohexane of at least 2% by weight at a pressure of 90 torr and a temperature of 24° C. It will also be appreciated that various other, different chemical corporations of an aluminophosphate nature, nevertheless having a similar composition and similar characteristics to such SAPO materials, as described in said patent application, may also be employed in the practice of the invention for the conversion of synthesis gas to hydrocarbons boiling in the gasoline and jet fuel and diesel oil boiling range.

The invention is hereinafter described with reference to certain specific examples that are presented herein to illustrate various embodiments, but that should not be construed as limiting the scope of the invention as set forth in the appended claims.

EXAMPLE 1

The following example, not constituting an embodiment of the invention, is presented as a reference for comparative purposes with respect to the examples of the invention to follow. In this example, a standard Fischer-Tropsch catalyst was employed under the process conditions of the invention, but without the co-action of a SAPO non-zeolitic molecular sieve catalyst as is in the practice of the invention. Thus, the composition of this example employs α-alumina as a non-molecular sieve co-catalyst/support component, it being readily appreciated that the presumably catalytically inert α-alumina, i.e., α-Al$_2$O$_3$, does not have the pore structure found in molecular sieve materials.

The Fischer-Tropsch metal component of the catalyst used in this example comprises iron precipitated with aqueous ammonia from a boiling solution of the nitrate salt. The resulting Fe$_2$O$_3$.xH$_2$O material was then impregnated with potassium carbonate and was physically mixed with 1μ particle size α-alumina polishing powder and pressed into pellets and calcined at 250° C. for two hours. Thus, the physical mixture of potassium-promoted iron and α-alumina was prepared by a conventional synthesis procedure providing a desirable reference with respect to other physical mixture catalyst compositions as hereinafter described.

The catalyst composition containing α-alumina as a co-catalyst/support component was employed for the conversion of syngas to hydrocarbons in an internal recirculation reactor with about 80 cc. of catalyst being employed in each run. The synthesis gas fed to the reactor in each case was composed of a mixture of carbon monoxide and hydrogen, together with argon in certain particular runs to facilitate computations of material balance and conversion. Thus, runs 1–5 in Table I, and runs 6–8 in Table II were carried out using a synthesis gas mixture of 50 mole % hydrogen and 50 mole % CO, while runs 9–10 in Table II and runs 1–3 in Table III employed a synthesis gas of 60% hydrogen, 30% CO and 10% argon, all in mole percent. The synthesis gas was fed to the reactor during each run at a rate of 300 GHSV, i.e. gas hourly space velocity, or volume of gas (at 0° C., 1 atm)/volume catalyst/hour.

The conversion reaction was carried out under substantially uniform processing conditions throughout the runs, with the reaction pressure being generally about 300 psig for each run and the reaction temperature being about 250° C. for runs 1–8 and about 280° C. for runs 9–13. Product samples of gas and liquid were collected over the course of the runs, with the liquid product generally having two layers, i.e., an aqueous layer and an organic oily layer, sometimes having contained solids or crystals associated therewith. The effluent gases were analyzed by gas chromatography for light hydrocarbons and fixed gases, e.g., hydrogen, CO, argon, CO$_2$ and the like.

Prior to syngas conversion, the catalyst composition was reduced or activated, in a conventional manner, by carbiding with a low H$_2$/CO ratio gas at a temperature of 250°–320° C. and a pressure of from 0 psig up to the synthesis operating pressure, and then subjecting the catalyst to hydrogen treatment under similar temperature and pressure conditions.

The results obtained in such reference runs in terms of the conversion of syngas, i.e. (CO+H$_2$), the primary product selectivity between hydrocarbons and CO$_2$, the hydrocarbon selectivity of the desirable C$_5$+ range and other supplemental product characterizations are shown in said Tables I, II and III below with respect to the various runs carried out using the physical mixture of potassium-promoted iron and α-alumina under the various operating conditions employed in each table.

TABLE I

| Run | 1 | 2 | 3 | 4 | 5 |
|---|---|---|---|---|---|
| Hours on Stream | 5.0 | 21.67 | 28.84 | 46.34 | 51.34 |
| Temperature, °C. | 250 | 251 | 251 | 251 | 251 |
| Feed, cc/min. | 400 | 400 | 400 | 400 | 400 |
| Conversion, wt. % | | | | | |
| on CO | 95.83 | 95.19 | 94.99 | 89.61 | 79.70 |
| on H$_2$ | 64.80 | 63.23 | 63.33 | 61.19 | 52.40 |
| on (CO + H$_2$) | 80.29 | 79.25 | 79.20 | 75.47 | 66.19 |
| Product Selectivity, wt. % | | | | | |
| CH$_4$ | 6.70 | 7.52 | 7.15 | 6.94 | 7.01 |
| C$_2$-C$_4$ | 31.26 | 32.15 | 30.67 | 27.93 | 26.76 |
| Total C$_1$-C$_4$ | 37.96 | 39.67 | 37.82 | 34.87 | 33.77 |
| C$_5$-420° F. | 46.03 | 44.68 | 43.31 | 45.06 | 43.43 |
| 420° F.-700° F. | 13.35 | 13.06 | 15.67 | 16.71 | 17.78 |
| 700° F.-end point | 2.67 | 2.59 | 3.20 | 3.36 | 5.03 |
| C$_5$-end point | 62.04 | 60.33 | 62.18 | 65.13 | 66.23 |
| Iso/normal mole ratio: | | | | | |
| C$_4$ | 0.1399 | 0.1338 | 0.1330 | 0.1194 | 0.1093 |
| C$_5$ | 0.1575 | 0.1540 | 0.1589 | 0.1733 | 0.1614 |
| C$_6$ | 0.1980 | 0.1989 | 0.2115 | 0.1862 | 0.1646 |

The additional runs set forth in Table II were carried out under similar conditions, but at a temperature of 281° C. in Runs 9 and 10 and with all of the runs carried out over the extended period of time indicated therein.

TABLE II

| Run | 6 | 7 | 8 | 9 | 10 |
|---|---|---|---|---|---|
| Hours on Stream | 70.59 | 74.74 | 93.74 | 100.74 | 117.24 |
| Temperature, °C. | 251 | 251 | 250 | 281 | 281 |
| Feed, cc/min. | 400 | 400 | 400 | 400 | 400 |
| Conversion, wt % | | | | | |
| on CO | 77.36 | 77.67 | 72.96 | 91.07 | 90.95 |
| on H$_2$ | 50.77 | 50.52 | 48.74 | 49.66 | 49.07 |
| on (CO + H$_2$) | 64.26 | 64.22 | 60.98 | 64.04 | 13.58 |
| Product Selectivity, wt % | | | | | |
| CH$_4$ | 7.25 | 6.92 | 7.03 | 10.54 | 10.55 |

TABLE II-continued

| Run | 6 | 7 | 8 | 9 | 10 |
|---|---|---|---|---|---|
| $C_2$–$C_4$ | 26.06 | 24.92 | 23.82 | 31.35 | 31.73 |
| Total | | | | | |
| $C_1$–$C_4$ | 33.31 | 31.84 | 30.85 | 41.89 | 42.28 |
| $C_5$–420° F. | 43.38 | 35.80 | 35.22 | 35.99 | 36.02 |
| 420° F.–700° F. | 18.27 | 21.43 | 22.60 | 13.85 | 13.58 |
| 700° F.–end point | 5.04 | 10.92 | 11.32 | 8.27 | 8.11 |
| $C_5$–end point | 66.69 | 68.16 | 69.15 | 58.11 | 57.72 |
| Iso/normal mole ratio: | | | | | |
| $C_4$ | 0.0978 | 0.1020 | 0.0969 | 0.1086 | 0.1048 |
| $C_5$ | 0.1530 | 0.1467 | 0.1491 | 0.1607 | 0.1573 |
| $C_6$ | 0.1812 | 0.1540 | 0.1803 | 0.2030 | 0.1939 |

The additional Runs 11–13 were carried out over the extended periods of time set forth in Table III, at a temperature of 281° C. and otherwise similar processing conditions.

TABLE III

| Run | 11 | 12 | 13 |
|---|---|---|---|
| Hours on Stream | 125.49 | 141.49 | 147.49 |
| Temperature, °C. | 281 | 281 | 281 |
| Feed, cc/min. | 400 | 400 | 400 |
| Conversion, wt. % | | | |
| on CO | 92.39 | 94.52 | 94.81 |
| on $H_2$ | 46.77 | 47.33 | 47.92 |
| on (CO + $H_2$) | 61.92 | 62.98 | 63.5 |
| Product Selectivity, wt. % | | | |
| $CH_4$ | 11.99 | 11.91 | 11.50 |
| $C_2$–$C_4$ | 36.47 | 35.99 | 35.64 |
| Total $C_1$–$C_4$ | 48.46 | 47.90 | 47.14 |
| $C_5$–420° F. | 39.66 | 40.37 | 39.98 |
| 420° F.–700° F. | 7.73 | 7.63 | 8.77 |
| 700° F.–end point | 4.15 | 4.10 | 4.10 |
| $C_5$–end point | 51.54 | 52.10 | 52.86 |
| Iso/normal mole ratio: | | | |
| $C_4$ | 0.1064 | 0.1060 | 0.1049 |
| $C_5$ | 0.1478 | 0.1464 | 0.1570 |
| $C_6$ | 0.2084 | 0.2065 | 0.2032 |

Those skilled in the art will appreciate that the gasoline end point is about 420° F., while the diesel oil end point is about 700° F. It will also be appreciated that 420°–700° F. hydrocarbon material comprises molecules with more carbon atoms than $C_{10}$ hydrocarbons up to about $C_{22}$ material. Hydrocarbon material in the $C_{22}$–$C_{28}$ range generally comprises heavy distillate material, with material above $C_{28}$ generally comprising wax.

It will be seen that the Fischer-Tropsch metal component of the invention was able to achieve high syngas conversion at a $H_2$:CO ratio of 1:1 at 250° C. The $H_2$/CO usage ratio, not shown directly in the tables, indicates that the catalyst could be effectively used with feed streams having an even lower $H_2$:CO ratio. While initial activity would be similar in such a case, this does not assure, however, that the catalyst would not be subject to relatively rapid deactivation under such circumstances. It will be noted that high syngas conversion was likewise obtained when the $H_2$:CO ratio was switched from 1:1 to 2:1. The $H_2$/CO usage ratio also increased as expected under said latter conditions.

The major effect of the co-catalyst/support component of the catalyst is reflected in the product selectivity achieved. It will be seen that the methane yield shown in the Tables is relatively low, but nevertheless slightly higher than has been encountered using iron catalysts alone under comparable process conditions. This variation is believed to be due to factors relating to the means for preparing the metal component, the synthesis conditions employed in the production of the subject catalyst compositions, and/or possibly the grinding necessary to form the physical mixture catalysts.

The $C_5$+ yield obtained was relatively good, accounting for almost 70% of the hydrocarbons produced by weight, although undersired wax buildup in the reactor was observed. The effect of the α-alumina component has little effect on the quality of the $C_5$+ product, i.e., the gasoline octane number of the liquid product. Analyses have indicated that the $C_4$'s are mainly olefinic, and that the condensed product thereof is also olefinic. In tests using the product run 8 as a representative sample, the $C_5$ paraffin product was found to be mainly n-pentane with little iso-pentane, the iso/normal ratio being similar to what has been observe using a Fischer-Tropsch iron catalyst alone. The actual chromatogram from ASTM simulated distillation of $C_5$+ product shows that not only are the $C_5$ paraffins dominated by the normal material, but that the entire range of liquid product is likewise dominated by normals.

It should be noted that such a high proportion of normals has two important effects on the quality of the $C_5$+ product. The first effect is a very poor octane number, e.g., 55 for the representative sample. Such material boiling in the gasoline boiling range thus requires extensive upgrading before it can be used as gasoline. The second effect relates to the heavier product, i.e., diesel oil. Straight chain products tend to pack well together and are solids at fairly high temperatures. The pour point of the $C_5$+ product obtained in the runs was above room temperature, and said product was solid coming out of the reactor. While the cetane index of the normals may be very high, the diesel oil fraction must nevertheless be dewaxed in order to lower the pour point before it can be effectively used as fuel.

The hydrocarbon product obtained in the runs of Example 1 is, therefore, very similar to the product obtained using an iron catalyst without the α-alumina co-catalyst/support component. The catalyst composition of the example had a somewhat greater tendency to produce lighter products than had previously been observed using iron alone, possibly as a result of a particle size effect.

EXAMPLE 2

For purposes of this Example, a SAPO-11 sample having a raw material $SiO_2/Al_2O_3$ ratio of 0.6/1 was prepared using dipropylamine as the template. The sample was then calcined in air at 550° C. for two hours. Potassium promoted, hydrated iron oxide was prepared as in Example 1. The catalyst composition was prepared by mixing equal (anhydrous) weights of the potassium-promoted iron oxide and SAPO-11 material. The resulting powder was pressed into tablets in a pellet mill and was calcined at 250° C. for two hours.

A total of 80 cc. of the catalyst was loaded into an internal recirculation reactor, and the catalyst was activated, prior to syngas treatment, by pretreatment with $H_2$:CO in an amount of 1200:400 cc/min. at 270° C. and 60 psig for 22 hours, after which the catalyst was further treated with 2,000 cc/min. of hydrogen for 24 hours. The pressure on the reactor was then increased to 300 psig, and the temperature was decreased to 250° C., after which a 1:1 $H_2$:CO syngas feed stream was passed to the reactor for conversion therein.

The synthesis gas feed by the reactor containing said physically mixed potassium-promoted iron and SAPO-11 catalyst composition was, in each run, a 50 mole % hydrogen, 50 mole % of carbon monoxide mixture. The synthesis gas was fed to the reactor during each run at a rate of about 300 GHSV, i.e., gas hourly space velocity, or volume of gas (at 0° C., 1 atom)/volume catalyst/hour. The conversion reaction was carried out under substantially uniform processing conditions throughout the runs, with the reaction pressure being generally about 300 psig. for each run, and the reaction temperature being about 250° C. for certain runs and about 280° C. for other runs as noted in the following tables. Product samples of gas and liquid were collected over the course of the runs, as in Example 1, with the liquid product generally having two layers, i.e., an aqueous layer and an organic oily layer. The effluent gases were analyzed by gas chromatography for light hydrocarbons and fixed gases, e.g., hydrogen, CO, argon, $CO_2$ and the like.

The results obtained in various runs carried out in accordance with the practice of the invention, using the dual catalyst composition comprising a physical mixture of potassium-promoted iron and said SAPO-11 under the various operating conditions indicated, are shown in Tables IV and V below.

TABLE IV

| Run | 1 | 2 | 3 | 4 |
|---|---|---|---|---|
| Hours on Stream | 2.50 | 26.41 | 49.24 | 91.91 |
| Temperature, °C. | 254 | 255 | 256 | 255 |
| Feed, cc/min. | 400 | 400 | 400 | 400 |
| Conversion, wt. % | | | | |
| on CO | 95.58 | 92.74 | 92.21 | 90.54 |
| on $H_2$ | 66.67 | 62.34 | 62.64 | 61.62 |
| on (CO + $H_2$) | 80.71 | 77.46 | 77.34 | 76.03 |

TABLE IV-continued

| Run | 1 | 2 | 3 | 4 |
|---|---|---|---|---|
| Product Selectivity | | | | |
| $CH_4$ | 13.22 | 14.04 | 14.86 | 16.54 |
| $C_2$-$C_4$ | 38.54 | 41.20 | 40.37 | 40.17 |
| Total $C_1$-$C_4$ | 51.76 | 55.30 | 55.23 | 56.71 |
| $C_5$-420°F. | 38.19 | 34.49 | 34.74 | 33.65 |
| 420° F.-700° F. | 7.81 | 7.94 | 7.79 | 7.53 |
| 700° F.-end point | 2.23 | 2.27 | 2.23 | 2.12 |
| $C_5$-end point | 48.24 | 44.70 | 44.77 | 43.19 |
| Iso/normal mole ratio: | | | | |
| $C_4$ | 0.3287 | 0.1000 | 0.0896 | 0.0717 |
| $C_5$ | 0.9389 | 0.2568 | 0.1925 | 0.1472 |
| $C_6$ | 3.8677 | 1.1340 | 0.9154 | 0.6495 |

The runs of Table V were carried out under generally similar conditions to those employed in Table IV above, but over the extended periods of time at a reaction temperature of 280°–281° C. indicated in said Table V.

TABLE V

| Run | 1 | 2 | 3 | 4 | 5 |
|---|---|---|---|---|---|
| Hours on Stream | 99.41 | 146.49 | 195.86 | 235.32 | 283.99 |
| Temperature, °C. | 280 | 280 | 281 | 281 | 281 |
| Feed, cc/min. | 400 | 400 | 400 | 400 | 400 |
| Conversion, wt. % | | | | | |
| on CO | 99.02 | 93.19 | 93.05 | 92.88 | 92.61 |
| on $H_2$ | 67.48 | 70.40 | 71.22 | 70.52 | 71.02 |
| on (CO + $H_2$) | 80.24 | 81.69 | 82.00 | 81.58 | 81.71 |
| Product Selectivity | | | | | |
| $CH_4$ | 15.93 | 16.35 | 17.98 | 19.57 | 20.25 |
| $C_2$-$C_4$ | 41.68 | 42.73 | 45.60 | 45.19 | 46.04 |
| Total $C_1$-$C_4$ | 57.61 | 59.08 | 63.58 | 64.76 | 66.29 |
| $C_5$-420° F. | 32.61 | 33.65 | 31.83 | 30.24 | 29.96 |
| 420° F.-700° F. | 7.04 | 6.00 | 3.83 | 3.89 | 3.23 |
| 700° F.-end point | 2.74 | 1.28 | 0.77 | 1.11 | 0.52 |
| $C_5$-end point | 42.39 | 40.92 | 36.42 | 35.24 | 33.71 |
| Iso/normal mode ratio: | | | | | |
| $C_4$ | 0.1162 | 0.1076 | 0.1113 | 0.1069 | 0.1101 |
| $C_5$ | 0.3145 | 0.4765 | 0.5890 | 0.5892 | 0.5485 |
| $C_6$ | 1.6193 | 2.1272 | 2.4723 | 2.3412 | 2.2246 |

By comparison with the results set forth in Tables I–III in which a mixture of potassium-promoted iron and α-alumina was employed, the metal component again, in the results of Tables IV and V, demonstrated high initial syngas conversion with characteristics similar to those obtained in Example 1. The increase in reaction temperature from about 250° C. to about 280° C. did not significantly alter the conversion obtained. This would be expected as the conversion is a characteristic of the metal component of the catalyst composition.

It will be noted, however, that the product distribution obtained in Example 2 is very different from that obtained in Example 1. The catalyst of Example 2 produced more gaseous hydrocarbons than are obtained using iron alone or using a physical mixture of iron and α-alumina. The methane yield is above 10% and increased steadily over the course of the runs. The total $C_5^+$ product, on the other hand, accounted for only about 50% of the total hydrocarbons produced and dropped to less than 35% by the end of the Run 5 at 281° C.

Almost all of the $C_5^+$ product produced in Example 2 boils in the gasoline range, with some diesel oil production but with very little heavier material produced. The liquid product was found to become more paraffinic with time at 250° C., but the liquid becomes more olefinic again at 280° C. and remains so through the extended run time. The liquid product is also highly isomerized throughout the extended run time, so that gasoline product produced therefrom should have a high octane number. While the yield of gasoline and diesel oil produced using the catalyst composition is not extraordinarily high, it is comparable with that produced by other iron-based catalysts. Quite significant and remarkable, however, is the superior quality of the gasoline produced due to the extent of isomerization achieved by the catalyst composition as compared with other iron-based catalysts. It should also be noted that, unlike Example 1, the condensed product from the reaction is a liquid and not a waxy solid. This is consistent with the pour point measurements made, wherein the diesel oil fraction of this Example 2 had a pour point of 20° F., whereas a lighter fraction from Example 1 had /volume catalyst/hour. The conversion reaction was carried out under substantially uniform processing conditions throughout the runs, with the reaction pressure being generally about 300 psig for each run. Product samples of gas and liquid were collected over the course of the runs, as in Examples 1 and 2 with the liquid product generally having two layers, i.e. an aqueous layer and an organic oily layer. The effluent gases were analyzed by gas chromatography for light hydrocarbons and fixed gases, e.g. hydrogen, CO, $CO_2$ and the like.

The results obtained in various runs carried out in accordance with the practice of the invention using the dual catalyst composition comprising a physical mixture of thorium—promoted cobalt and said SAPO-11 under the various operating conditions indicated, are shown in Table VI below.

TABLE VI

| Run | 1 | 2 | 3 | 4 | 5 |
|---|---|---|---|---|---|
| Hours on Stream | 30 | 72 | 102 | 167 | 191 |
| Temperature, °C. | 273 | 269 | 269 | 269 | 269 |
| Feed, cc/min. | 400 | 400 | 400 | 400 | 400 |
| Conversion, wt. % | | | | | |
| on CO | 67.95 | 57.10 | 53.48 | 49.61 | 48.40 |
| on $H_2$ | 93.05 | 90.65 | 84.74 | 80.20 | 78.54 |
| on (CO + $H_2$) | 81.03 | 74.44 | 64.47 | 65.36 | 63.96 |
| Product Selectivity | | | | | |
| $CH_4$ | 16.73 | 16.56 | 19.90 | 23.78 | 24.23 |
| $C_2$-$C_4$ | 13.44 | 12.21 | 14.13 | 14.61 | 15.65 |
| Total $C_1$-$C_4$ | 30.17 | 28.77 | 34.03 | 38.39 | 39.88 |
| $C_5$-420° F. | 46.10 | 45.76 | 44.04 | 39.71 | 40.02 |
| 420° F.-700° F. | 21.59 | 23.07 | 19.61 | 19.42 | 17.60 |
| 700° F.-end point | 2.14 | 2.40 | 2.32 | 2.47 | 2.50 |
| $C_5$-end point | 69.83 | 71.23 | 65.97 | 61.61 | 60.12 |
| Iso/normal mole ratio: | | | | | |
| $C_4$ | 0.0439 | 0.0351 | 0.0313 | 0.0309 | 0.0311 |
| $C_5$ | 0.1243 | 0.0838 | 0.0941 | 0.0908 | 0.0920 |
| $C_6$ | 0.2148 | 0.1421 | 0.1424 | 0.1424 | 0.1448 | a pour point of 65° F. The product of this example, therefore, requires less, if any, dewaxing as compared with said Example 1 product before being used as a motor fuel.

EXAMPLE 3

In this Example, a SAPO-11 sample having a $SiO_2$/$Al_2O_3$ ratio of 1/1 was prepared using dipropylamine and methanolic tetrabutylammonium hydroxide as the templates. The sample was then calcined in air at 550° C. for two hours. Hydrated cobalt oxide was prepared by precipitation, upon addition of a 5% excess over the stoichiometric amount of sodium carbonate to a stirred solution of cobalt nitrate. The precipitated cobalt oxide was dried at 110° C., impregnated with thorium nitrate and dried again at 110° C. The cobalt, SAPO-11 and silica binder were combined at a weight ratio of 15:70:15 and the mixture was formed as ⅛" extrudate that was subsequently calcined at 250° C. for two hours.

A total of 80 cc of the catalyst was loaded into an internal recirculation reactor, and the catalyst was activated by being heated to 350° C. in the presence of hydrogen passed to the reactor at 300 psig and at a rate of 1,000 cc/min. The catalyst was then held at 350° C. for 24 hours and was then cooled to 270° C. for treatment with a 1:1$H_2$:CO syngas feed stream at that temperature level.

The synthesis gas fed to the reactor was, in each run, a 50 mole % hydrogen, 50 mole % carbon monoxide mixture. The synthesis gas was fed to the reactor during each run at a rate of about 300 GHSV, i.e. gas hourly space velocity, or volume of gas (at 0° C. 1 atm)-

It was found that the methane production is not as high as that typically produced by a standard Fischer-Tropsch cobalt catalyst under essentially the same operating conditions. The condensed product contained in the runs of Example 3 was a liquid as opposed to the waxy solid containing condensed product that is produced using standard cobalt catalysts. While the pentane produced is not highly isomerized, the fact that the condensed product is a liquid indicates that the double bonds of the heavier olefin products are isomerized. The pour point of the diesel fraction was found to be even lower than in Example 2, i.e. 10° F., indicating an even less waxy product than was obtained in said Example 2. It will be appreciated from the results above that the embodiment of the invention demonstrates an advantageous conversion of syngas to desired liquid motor fuels, with relatively minor amounts of heavy products boiling beyond the diesel oil range having been produced. The quality of motor fuels produced in the $C_{10}$-$C_{18}$ range, in terms of branched hydrocarbons suitable for jet and diesel fuels is improved, and the quality of the gasoline produced is superior to the Example 1 product due to the isomerization activity referred to above.

Those skilled in the art will appreciate that various changes and modifications can be made in the details of the invention as herein described and illustrated without departing from the scope of the invention as set forth in the appended claims. Thus, the conversion of syngas to $C_5$+ hydrocarbon mixtures containing more than 10%, typically more than 20% and commonly more than 50% or even more than 70% of $C_5+$ hydrocarbon molecules comprising $C_5$ up to about $C_{22}$ material is advantageously accomplished in a variety of embodiments wherein the catalyst composition comprises a Fischer-Tropsch catalyst together with a SAPO co-catalyst/support component as herein described. The product obtained using the novel catalyst composition of the invention contains enhanced amounts of isomerized hydrocarbons in addition to n-paraffins and n-α-olefins. While appreciable amounts of methane have been produced in the practice of various embodiments of the invention, it is of significance that only relatively minor amounts of heavy products boiling beyond the diesel oil range are produced. The syngas is thus advantageously converted to hydrocarbons boiling in the gasoline and in the jet fuel and diesel oil range, with particularly high quality gasoline range material being produced. Such conversion reaction can be carried out under any suitable operating conditions, with the reaction temperature being generally from about 100° C. to about 400° C., generally from about 150° C. to about 400° C. using cobalt-containing catalyst, and from about 200° C. to about 400° C. when iron-containing catalyst is employed, preferably from about 220° C. to about 320° C. The catalytic conversion reaction is carried out at any desired pressure level, for example at pressures of from about 0 to about 1,000 psig, typically at from about 0 to about 350 psig.

The catalyst composition of the invention can be prepared in any suitable manner known in the art. Thus, Fischer-Tropsch metal can be precipitated or pore-filled on the co-catalyst/support component, or a physical mixture of said components can be prepared, as in the illustrative examples above. The amount of said Fischer-Tropsch metal component employed in any particular application of the invention will depend upon the desired operating conditions and particular product specifications pertaining to that application. In general, however, the metal component will be employed in an amount with the range of from about 5% to about 70% by weight based on the overall weight of the catalyst composition, with metal component concentrations of from about 10% to about 50% being generally preferred in most applications. The activating of the Fischer-Tropsch metal component prior to use of the catalyst is carried out by conventional techniques known in the art, such as the technique referred to with respect to the examples above. Thus, Fischer-Tropsch synthesis catalysts are commonly reduced or activated initially with hydrogen or a hydrogen-containing gas at a temperature on the order of 450° C. or lower and at a pressure of from 0 psig up to the synthesis gas operating pressure. The catalysts can then be subjected to carbiding with a low $H_2/CO$ ratio gas at a temperature up to the desired synthesis operating temperature. Alternatively, it is also possible to activate the catalyst by carbiding first with low $H_2/CO$ ratio gas, or with CO alone, at a temperature in the range of about 250°–320° C. and a pressure of from 0 psig to the synthesis operating pressure, followed by hydrogen treatment at a similar temperature and pressure. Further information regarding the preparation and activation of Fischer-Tropsch catalysts is provided in the published art, as in CATAL.-REV.-SCI.ENG., 21(2), 225–274 (1980). "The Fischer-Tropsch Synthesis in the Liquid Phase", by Herbert Kolbel and Miles Ralek, particularly pp. 242–247 thereof.

It will be appreciated by those skilled in the art that the catalyst composition of the invention may, as in the examples above, have a suitable promoter component incorporated therein. Potassium, sodium and thorium are examples of known promoters, with potassium being a generally preferred promoter for iron catalysts, while thorium is generally preferred for cobalt catalysts, as employed in the syngas conversion operations of the invention. This promotion can readily be accomplished by impregnating the metal-loaded SAPO molecular sieve with a potassium or thorium salt solution prior to drying and calcining. For example, a physical mixture of iron and SAPO molecular sieve, promoted with potassium, is conveniently prepared from a refluxing solution of 0.05 g/ml of ferric nitrate solution. Iron powder comprising $Fe_2O_3 \times H_2O$ is first precipitated by the addition of a stoichiometric amount of 6N aqueous ammonia. The resulting powder is collected, washed with hot distilled water, e.g. at about 95° C., and dried at 110° C. overnight. The iron powder is then impregnated with $K_2CO_3$ solution and dried. The potassium-promoted catalysts of the examples will contain about 0.7 wt.% $K_2O$ although it will be appreciated that the concentration of potassium or other promoter employed will vary depending upon the Fischer-Tropsch metal and the promoter employed in any particular embodiment. The potassium-promoted, precipitated iron powder can be ground slightly, mixed with an equal weight of SAPO material, pressed into pellets, and air calcined at 250° C. for two hours to produce a metal and co-catalyst support composition comprising a physical mixture of promoted said iron and said SAPO molecular sieve containing about 53% iron by weight. The effects of potassium or other promotion are believed to include the introduction of water gas shift activity to the catalyst composition so as to reduce the $H_2/CO$ usage ratio and achieve greater overall syngas conversion. This effect of such promotion appears to be greater with respect to physical mixtures of the catalyst composition than is the case when the Fischer-Tropsch metal component is precipitated on the co-catalyst/support component of the catalyst composition. The potassium-promoted catalysts will in general have a potassium concentration of from about 0.1 to about 5 wt. percent of $K_2O$ with sodium-promoted catalysts having a similar concentration range and thorium-promoted catalysts having such a concentration extended up to about 15%.

In the pore-filled catalyst compositions referred to above, the Fischer-Tropsch metal component resides mainly in the large pores between the SAPO adsorbent particles. In another highly advantageous embodiment of the invention, the Fischer-Tropsch metal component is supported inside the crystal structure of a steam-stabilized, hydrophobic zeolite Y employed as an additional co-catalyst/support component. Such zeolite Y compositions have been referred to in the art as ultrahydrophobic Type Y zeolites, or simply as UHP-Y zeolites. The Y zeolites used in this embodiment of the invention are prepared by steaming of the low-sodium forms of zeolite Y substantially as described in Belgium Pat. No. 874,373, issued Feb. 22, 1979. Such zeolites are organophilic zeolitic aluminosilicate compositions having a $SiO_2/Al_2O_3$ molar ratio equal to or greater than 4.5, and an essential X-ray powder diffraction pattern of zeolite Y. Furthermore, the zeolites have a crystallographic unit cell dimension, $a_o$, of less than 24.45 Angstoms, a sorptive capacity of water vapor at 25° C. and a $p/p_o$ value of 0.10 of less than 10.0 weight percent. In preferred compositions, said unit cell dimensions of the catalysts is from 24.20 to 24.35 Angstroms. In addition, the water adsorption capacity at 25° C. and a $p/p_o$ value of 0.10 is desirably less than 6.0 or even less than 4.0 weight percent. More particularly the $SiO_2/Al_2O_3$ molar ratio for certain embodiments is from 4.5 to 20.0. In a particularly desirable embodiment in which the UHP-Y zeolite is acid extracted, the $SiO_2/Al_2O_3$ molar ratio may be extended up to about 100 or more, as the alumina content of the zeolite is generally reduced to less than about 3 weight % or even to about 1 weight-% or less in practical commercial operations.

In the embodiments in which such a commercially available UHP-Y zeolite is employed as an additional co-catalyst/support component, the Fischer-Tropsch catalyst, i.e. metal component, may be pore-filled so as to reside mainly in the large pores between the UHP-Y zeolite particles. It has also been found possible to place the metal component within the crystallites of the UHP-Y zeolite or of said aluminum extracted, or acid extracted, UHP-Y zeolite referred to above. For this purpose, the zeolite may be acid washed or extracted essentially by the process as described in the Eberly patent, U.S. Pat. No. 3,591,488, to remove a large portion of the alumina from its pores prior to treatment to incorporate the metal component therein. By employing a suitable metal-containing liquid, such as an iron, cobalt or other suitable metal carbonyl or a salt solution, such as a metal nitrate, the metal can be positioned substantially within the crystals, and adsorbed therein to form a co-catalyst/support composition highly advantageous for purposes of the invention. In an illustrative example, UHP-Y molecular sieve zeolite was refluxed in a 13% slurry of said sieve in 3.75M hydrochloric acid for three hours. The slurry was then cooled, and the supernatent was decanted therefrom. The remaining slurry was diluted in half, filtered and washed chloride-free with 0.001M nitric acid. The slurry was then washed with distilled water, dried at 110° C. for 16 hours and then at 250° C. for 16 hours and at 500° C. for an additional two hours and bottled at 400° C. The thus treatment material comprises acid-extracted substantially alumina-free, or aluminum extracted, UHP-Y zeolite.

For purposes of positioning the metal component within the crystals of the UHP-Y zeolite or the acid-extracted form thereof, said zeolite can be loaded with liquid iron carbonyl, i.e. $Fe(CO)_5$, by impregnation under nitrogen to form a material containing approximately 28% $Fe(CO)_5$-loaded UHP-Y zeolite can be heated to 120° C. in a stream of 0.5% oxygen in nitrogen for three hours, and then at 200° C. for an additional hour. The resulting metal component having the iron positioned within the crystals of the zeolite is conveniently combined with a SAPO component and formed as $\frac{1}{8}"$ extrudate using 15% silica and 3% KOH as a gelling agent and avicel as an extrusion aid. The extrudates thus formed can be dried at 110° C. and calcined at 250° C.

In the practice of the invention, the supporting of the Fischer-Tropsch catalyst inside the crystals of a steam-stabilized, hydrophobic zeolite Y, employed as an additional co-catalyst/support component enhances the performance of the syngas conversion operation and the desired production of appreciable quantities of $C_5+$ hydrocarbon molecules. Thus, such a use of a UHP-Y zeolite as a co-catalyst/support component, in combination with a Fischer-Tropsch metal component, such as cobalt, together with a SAPO co-catalyst/support component, e.g. SAPO-11 or SAPO-31, represents a very desirable embodiment of the invention. The catalyst formed by loading the aluminum-extracted form of said UHP-Y zeolite from a liquid metal-containing material, and believed to have said metal component positioned within the pores of the zeolite itself, has remarkable stability extending over long periods of time. It will be appreciated, therefore, that the use of an aluminum extracted UHP-Y zeolite, typically having an alumina content of less than 3 weight %, in combination with a Fischer-Tropsch metal component, e.g. cobalt or iron, together with a silicoaluminophosphate co-catalyst/support component, e.g. SAPO-11 or SAPO-31, represents a preferred embodiment of the catalyst composition described and claimed herein for advantageous conversion of syngas to any hydrocarbons boiling in the gasoline and jet and diesel oil boiling range.

In the acid extraction of the zeolite, as employed in preferred embodiments of the invention, those skilled in the art will appreciate that this pretreatment step is carried out using the process known in the art in a manner that is not destructive of the zeolite structure as characterized by X-ray diffraction and by adsorption measurements. In addition to the hydrochloric acid extraction of the zeolite as indicated above, it is within the scope of this aspect of the invention to similarly wash the zeolite with nitric acid or other suitable mineral acids, or with other complexing agents, such EDTA, i.e. ethylene diamine tetraacetic acid, and the like. As indicated above, the alumina content of the zeolite is typically reduced to less than about 3 weight % or even to about 1 weight % or less based on the overall weight of said thus-treated zeolite, in said aluminum extraction step.

It will also be appreciated that the addition of the Fischer-Tropsch metal component to the acid-extraction zeolite can be accomplished by any known metal loading technique capable of enabling a significant amount of said metal component to be deposited in the co-catalyst/support component, advantageously in the pores of the acid-extracted zeolite itself. In addition to the carbonyl adsorption technique referred to above, using cobalt or iron or other suitable carbonyls, it should be noted that other known techniques are suitable for loading the metal component on the acid-extracted UHP-Y zeolite. Such techniques include metal salt impregnation, as with ferric, cobalt or other suitable nitrates, chlorides, cyanides or the like; metal organic impregnation, as with iron methylcyclopentadienyldicarbonyl and the like; and other known metal loading means, such as by ion exchange means. The highly preferred embodiments of the invention in which the additional co-catalyst/support component comprises said zeolite Y in acid-extracted form, with the catalyst component loaded thereon, and advantageously positioned substantially or mainly within the pores of said acid-extracted zeolite, can thus be prepared by use of a variety of known acid wash and metal loading techniques. As indicated above, the resulting catalyst compositions exhibit remarkably enhanced stability when employed for the desired synthesis gas conversion purpose wherein only relatively minor amounts of heavy products boiling beyond the diesel oil range are produced.

The invention as herein described and claimed provides a highly desirable advance in the art of employing Fischer-Tropsch metals in the conversion of syngas to hydrocarbon products. By employing such Fischer-Tropsch metals in combination with a co-catalyst/support component comprising a crystalline microporous SAPO silicoaluminophosphate, non-zeolite molecular sieve catalyst, it has been found possible to advantageously convert syngas to hydrocarbons boiling in the gasoline plus jet fuel and diesel oil boiling range. The syngas conversion process of the invention can be carried out using the novel catalyst composition disclosed and claimed so as to produce such desired liquid motor fuels while producing only relatively minor amounts of heavy products boiling beyond the diesel oil range. Particularly advantageous results have been obtained using the catalyst composition of the invention in combination with an additional co-catalyst/support component comprising a steam-stabilized, zeolite Y catalyst of hydrophobic character as described and claimed herein, particularly in the aluminum extracted form of said zeolite. The invention enables the product hydrocarbon molecules comprising $C_{10}$ up to $C_{22}$ material to contain useful amounts of the branched hydrocarbons needed for such fuels. The invention thus enables syngas to be converted to high quality gasoline and other desirable liquid motor fuels in a convenient and practical manner. The invention thereby fulfills a significant need in the syngas conversion art and provides a highly advantageous approach to the satisfying of the increasing motor fuel requirements of industrialized countries throughout the world.

We claim:

1. A catalyst composition adapted for the enhanced conversion of synthesis gas comprising carbon monoxide and hydrogen to $C_5+$ hydrocarbon mixtures having enhanced suitability for use as liquid motor fuels comprising:
   (a) a Fischer-Tropsch catalyst component; and
   (b) a co-catalyst/support component comprising a crystalline, microporous silicoaluminophosphate, non-zeolitic molecular sieve catalyst,
whereby said catalyst composition is capable of enhancing the selectivity of said conversion to motor fuel range hydrocarbons and the quality of the resulting motor fuel product.

2. The composition of claim 1 in which said silicoaluminophosphate catalyst comprises SAPO-11.

3. The composition of claim 1 in which said silicoaluminophosphate catalyst comprises SAPO-31.

4. The composition of claim 1 in which said Fischer-Tropsch catalyst comprises cobalt.

5. The composition of claim 1 in which said Fischer-Tropsch catalyst comprises iron.

6. The composition of said claim 2 in which said Fischer-Tropsch catalyst comprises cobalt.

7. The composition of claim 3 in which said Fischer-Tropsch catalyst comprises cobalt.

8. The composition of claim 2 in which said Fischer-Tropsch catalyst comprises iron.

9. The composition of claim 3 in which said Fischer-Tropsch catalyst comprises iron.

10. The composition of claim 1 and including a steam-stabilized, hydrophobic zeolite Y additional co-catalyst/support component, said Fischer-Tropsch catalyst being supported mainly inside the crystals of said zeolite Y component.

11. The composition of claim 10 in which said Fischer-Tropsch catalyst comprises cobalt.

12. The composition of claim 11 in which said silicoaluminophosphate catalyst comprises SAPO-11.

13. The composition of claim 11 in which said silicoaluminophosphate catalyst comprises SAPO-31.

14. The composition of claim 10 in which said Fischer-Tropsch catalyst comprises iron.

15. The composition of claim 14 in which said silicoaluminophosphate catalyst comprises SAPO-11.

16. The composition of claim 14 in which said silicoaluminophosphate catalyst comprises SAPO-31.

17. The composition of claim 10 in which said zeolite Y component is in aluminum-extracted form.

18. The composition of claim 17 in which the alumina content of said aluminum-extracted zeolite is less than about 3 weight %.

19. The composition of claim 18 in which said Fischer-Tropsch catalyst comprises cobalt or iron and said silicoaluminophosphate catalyst comprises SAPO-11.

20. The composition of claim 18 in which said Fischer-Tropsch catalyst comprises cobalt or iron and said silicoaluminophosphate catalyst comprises SAPO-31.

21. The composition of claim 10 in which said zeolite Y has an $SiO_2/Al_2O_3$ molar ratio equal to or greater than 4.5, the essential X-ray powder diffraction pattern of zeolite Y, a unit cell dimension, $A_o$, of less than 24.45 Angstroms, and a sorptive capacity for water vapor at 25° C. and a $p/p_o$ value of 0.10 of less than 10.0 weight percent.

22. The composition of claim 21 in which said $SiO_2/Al_2O_3$ molar ratio of the catalyst is from 4.5 to 9.0, and in which said unit cell dimension is from 24.20 to 24.45 Angstroms.

23. The composition of claim 19 in which the water adsorption capacity of the catalyst, at 25° C. and a $p/p_o$ of 0.10, is less than 6.0 weight percent.

24. The composition of claim 18 in which said zeolite Y has an $SiO_2/Al_2O_3$ molar ratio equal to a greater than 4.5, the essential X-ray powder diffraction pattern of zeolite Y, a unit cell dimension, $A_o$, of less than 24.45 Angstroms, and a sorptive capacity for water vapor at 25° C. and a $p/p_o$ value of 0.10 of less than 10.0 weight percent.

25. The composition of claim 1 in which said silicoaluminophosphate comprises catalyst characterized by an adsorption of triethylamine of less than 5% by weight at a pressure of 2.6 torr and a temperature of 22° C.

26. The composition of claim 1 in which said silicoaluminophosphate comprises catalyst further characterized by an adsorption of cyclohexane of at least 2% by weight at a pressure of 90 torr and a temperature of 24° C.

27. The composition of claim 25 in which said Fischer-Tropsch catalyst comprises cobalt.

28. The composition of claim 26 in which said Fischer-Tropsch catalyst comprises iron.

29. The composition of claim 10 in which said silicoaluminophosphate comprises catalyst characterized by an adsorption of triethylamine of less than 5% by weight at a pressure of 2.6 torr and a temperature of 22° C.

30. The composition of claim 29 in which said silicoaluminophosphate comprises catalyst further characterized by an adsorption of cyclohexane of at least 2% by weight at a pressure of 90 torr and a temperature of 24° C.

31. The composition of claim 29 in which said zeolite Y compound is in aluminum-extracted form.

32. The composition of claim 29 in which said aluminia content of said aluminum-extracted zeolite is less than about 3 weight %.

* * * * *

UNITED STATES PATENT AND TRADEMARK OFFICE
CERTIFICATE OF CORRECTION

PATENT NO. : 4,556,645

DATED : December 3, 1985

INVENTOR(S) : Peter K. Coughlin, et al

It is certified that error appears in the above-identified patent and that said Letters Patent is hereby corrected as shown below:

Col. 2, line 16, "as" should read -- an --.

Col. 7, Table III, line 11, under heading 13, "63.5" should read -- 63.57 --.

Col. 8, line 21, "undersired" should read -- undesired --.

Signed and Sealed this

Eleventh Day of March 1986

[SEAL]

Attest:

Attesting Officer

DONALD J. QUIGG

Commissioner of Patents and Trademarks